United States Patent
Knapp et al.

(10) Patent No.: US 11,684,362 B2
(45) Date of Patent: Jun. 27, 2023

(54) HANDHELD ELECTROMECHANICAL SURGICAL SYSTEM

(71) Applicant: Covidien LP, Mansfield, MA (US)

(72) Inventors: Robert H. Knapp, Middlebury, CT (US); Alexander J. Hart, Tolland, CT (US); Alexander W. Caulk, Trumbull, CT (US); Haley E. Strassner, Hamden, CT (US)

(73) Assignee: Covidien LP, Mansfield, MA (US)

( * ) Notice: Subject to any disclaimer, the term of this patent is extended or adjusted under 35 U.S.C. 154(b) by 39 days.

(21) Appl. No.: 17/340,385

(22) Filed: Jun. 7, 2021

(65) Prior Publication Data

US 2022/0387022 A1 Dec. 8, 2022

(51) Int. Cl.
*A61B 17/068* (2006.01)
*A61B 17/072* (2006.01)
*A61B 17/00* (2006.01)

(52) U.S. Cl.
CPC ........ *A61B 17/0686* (2013.01); *A61B 17/072* (2013.01); *A61B 2017/00199* (2013.01);
(Continued)

(58) Field of Classification Search
CPC .............. A61B 17/0686; A61B 17/072; A61B 2017/00199; A61B 2017/00398; A61B 2017/07257; A61B 2017/07271
(Continued)

(56) References Cited

U.S. PATENT DOCUMENTS

| 37,165 A | 12/1862 | Gary |
| 3,209,754 A | 10/1965 | Brown |

(Continued)

FOREIGN PATENT DOCUMENTS

| CN | 101683284 A | 3/2010 |
| CN | 102648864 A | 8/2012 |

(Continued)

OTHER PUBLICATIONS

Detemple, P., "Microtechnology in Modern Health Care", Med Device Technol. 9(9):18-25 (1998).
(Continued)

*Primary Examiner* — Dariush Seif
(74) *Attorney, Agent, or Firm* — Carter, DeLuca & Farrell LLP

(57) ABSTRACT

A surgical device includes a handle assembly having: a power source, a motor coupled to the power source, and a controller configured to control the motor. The device also includes an adapter assembly configured to selectively couple to the handle assembly. The adapter assembly includes a clamping transmission assembly movable by the motor. The device also includes a reload configured to selectively couple to a distal portion of the adapter assembly, the reload including a plurality of staples ejectable from the reload. The device further includes an anvil assembly selectively couplable to the distal portion of the adapter assembly and movable relative to the reload. The controller is further configured to control the motor to move the clamping transmission assembly to move the anvil assembly from a distal clamp position to a proximal clamp position and then distally from the proximal clamp position to reduce clamp force.

18 Claims, 10 Drawing Sheets

(52) U.S. Cl.
CPC ............... *A61B 2017/00398* (2013.01); *A61B 2017/07257* (2013.01); *A61B 2017/07271* (2013.01)

(58) Field of Classification Search
USPC .............. 227/175.1–182.1; 606/75, 219, 220
See application file for complete search history.

(56) References Cited

U.S. PATENT DOCUMENTS

| | | |
|---|---|---|
| 3,273,562 A | 9/1966 | Brown |
| 3,499,591 A | 3/1970 | Green |
| 3,528,693 A | 9/1970 | Pearson et al. |
| 3,744,495 A | 7/1973 | Johnson |
| 3,862,631 A | 1/1975 | Austin |
| 3,949,924 A | 4/1976 | Green |
| 4,060,089 A | 11/1977 | Noiles |
| 4,204,623 A | 5/1980 | Green |
| 4,217,902 A | 8/1980 | March |
| 4,263,903 A | 4/1981 | Griggs |
| 4,275,813 A | 6/1981 | Noiles |
| 4,331,277 A | 5/1982 | Green |
| 4,428,376 A | 1/1984 | Mericle |
| 4,429,695 A | 2/1984 | Green |
| 4,444,181 A | 4/1984 | Wevers et al. |
| 4,454,875 A | 6/1984 | Pratt et al. |
| 4,456,006 A | 6/1984 | Wevers et al. |
| 4,485,816 A | 12/1984 | Krumme |
| 4,485,817 A | 12/1984 | Swiggett |
| 4,488,523 A | 12/1984 | Shichman |
| 4,508,253 A | 4/1985 | Green |
| 4,508,523 A | 4/1985 | Leu |
| 4,522,206 A | 6/1985 | Whipple et al. |
| 4,534,350 A | 8/1985 | Golden et al. |
| 4,535,772 A | 8/1985 | Sheehan |
| 4,566,620 A | 1/1986 | Green et al. |
| 4,570,623 A | 2/1986 | Ellison et al. |
| 4,606,343 A | 8/1986 | Conta et al. |
| 4,606,344 A | 8/1986 | Di Giovanni |
| 4,610,383 A | 9/1986 | Rothfuss et al. |
| 4,612,923 A | 9/1986 | Kronenthal |
| 4,612,933 A | 9/1986 | Brinkerhoff et al. |
| D286,442 S | 10/1986 | Korthoff et al. |
| 4,627,437 A | 12/1986 | Bedi et al. |
| 4,635,637 A | 1/1987 | Schreiber |
| 4,662,371 A | 5/1987 | Whipple et al. |
| 4,671,280 A | 6/1987 | Dorband et al. |
| 4,705,038 A | 11/1987 | Sjostrom et al. |
| 4,712,550 A | 12/1987 | Sinnett |
| 4,719,917 A | 1/1988 | Barrows et al. |
| 4,724,839 A | 2/1988 | Bedi et al. |
| 4,731,058 A | 3/1988 | Doan |
| 4,805,617 A | 2/1989 | Bedi et al. |
| 4,807,628 A | 2/1989 | Peters et al. |
| 4,852,558 A | 8/1989 | Outerbridge |
| 4,913,144 A | 4/1990 | Del Medico |
| 4,960,420 A | 10/1990 | Goble et al. |
| 4,962,877 A | 10/1990 | Hervas |
| 4,990,153 A | 2/1991 | Richards |
| 4,994,073 A | 2/1991 | Green |
| 4,995,877 A | 2/1991 | Ams et al. |
| 5,040,715 A | 8/1991 | Green et al. |
| 5,065,929 A | 11/1991 | Schulze et al. |
| 5,089,009 A | 2/1992 | Green |
| 5,108,422 A | 4/1992 | Green et al. |
| 5,114,399 A | 5/1992 | Kovalcheck |
| 5,129,570 A | 7/1992 | Schulze et al. |
| 5,143,453 A | 9/1992 | Weynant nee Girones |
| 5,203,864 A | 4/1993 | Phillips |
| 5,207,697 A | 5/1993 | Carusillo et al. |
| 5,209,756 A | 5/1993 | Seedhom et al. |
| 5,246,443 A | 9/1993 | Mai |
| 5,258,008 A | 11/1993 | Wilk |
| 5,271,543 A | 12/1993 | Grant et al. |
| RE34,519 E | 1/1994 | Fox et al. |
| 5,282,829 A | 2/1994 | Hermes |
| 5,300,081 A | 4/1994 | Young et al. |
| 5,307,976 A | 5/1994 | Olson et al. |
| 5,312,023 A | 5/1994 | Green et al. |
| 5,312,024 A | 5/1994 | Grant et al. |
| 5,313,935 A | 5/1994 | Kortenbach et al. |
| 5,318,221 A | 6/1994 | Green et al. |
| 5,326,013 A | 7/1994 | Green et al. |
| 5,330,486 A | 7/1994 | Wilk |
| 5,332,142 A | 7/1994 | Robinson et al. |
| 5,342,376 A | 8/1994 | Ruff |
| 5,350,355 A | 9/1994 | Sklar |
| 5,356,064 A | 10/1994 | Green et al. |
| 5,359,993 A | 11/1994 | Slater et al. |
| 5,364,001 A | 11/1994 | Bryan |
| 5,381,943 A | 1/1995 | Allen et al. |
| 5,383,874 A | 1/1995 | Jackson et al. |
| 5,383,880 A | 1/1995 | Hooven |
| 5,389,098 A | 2/1995 | Tsuruta et al. |
| 5,391,166 A | 2/1995 | Eggers |
| 5,395,030 A | 3/1995 | Kuramoto et al. |
| 5,395,033 A | 3/1995 | Byrne et al. |
| 5,400,267 A | 3/1995 | Denen et al. |
| 5,403,312 A | 4/1995 | Yates et al. |
| 5,405,344 A | 4/1995 | Williamson et al. |
| 5,411,508 A | 5/1995 | Bessler et al. |
| 5,413,267 A | 5/1995 | Solyntjes et al. |
| 5,431,323 A | 7/1995 | Smith et al. |
| 5,464,144 A | 11/1995 | Guy et al. |
| 5,467,911 A | 11/1995 | Tsuruta et al. |
| 5,478,344 A | 12/1995 | Stone et al. |
| 5,482,100 A | 1/1996 | Kuhar |
| 5,484,095 A * | 1/1996 | Green ................ A61B 17/0686 227/181.1 |
| 5,485,947 A | 1/1996 | Olson et al. |
| 5,487,499 A | 1/1996 | Sorrentino et al. |
| 5,497,933 A | 3/1996 | DeFonzo et al. |
| 5,500,000 A | 3/1996 | Feagin et al. |
| 5,503,320 A | 4/1996 | Webster et al. |
| 5,507,743 A | 4/1996 | Edwards et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,531,744 A | 7/1996 | Nardella et al. |
| 5,533,661 A | 7/1996 | Main et al. |
| 5,535,934 A | 7/1996 | Boiarski et al. |
| 5,535,937 A | 7/1996 | Boiarski et al. |
| 5,558,671 A | 9/1996 | Yates |
| 5,560,532 A | 10/1996 | DeFonzo et al. |
| 5,562,239 A | 10/1996 | Boiarski et al. |
| 5,571,285 A | 11/1996 | Chow et al. |
| 5,575,799 A | 11/1996 | Bolanos et al. |
| 5,582,611 A | 12/1996 | Tsuruta et al. |
| 5,584,835 A | 12/1996 | Greenfield |
| 5,601,224 A | 2/1997 | Bishop et al. |
| 5,601,558 A | 2/1997 | Torrie et al. |
| 5,607,095 A | 3/1997 | Smith et al. |
| 5,609,285 A | 3/1997 | Grant et al. |
| 5,609,560 A | 3/1997 | Ichikawa et al. |
| 5,624,452 A | 4/1997 | Yates |
| 5,632,433 A | 5/1997 | Grant et al. |
| 5,634,926 A | 6/1997 | Jobe |
| 5,642,848 A | 7/1997 | Ludwig et al. |
| 5,653,374 A | 8/1997 | Young et al. |
| 5,658,300 A | 8/1997 | Bito et al. |
| 5,658,312 A | 8/1997 | Green et al. |
| 5,662,662 A | 9/1997 | Bishop et al. |
| 5,665,085 A | 9/1997 | Nardella |
| 5,667,513 A | 9/1997 | Torrie et al. |
| 5,667,517 A | 9/1997 | Hooven |
| 5,667,527 A | 9/1997 | Cook |
| 5,669,544 A | 9/1997 | Schulze et al. |
| 5,673,841 A | 10/1997 | Schulze et al. |
| 5,676,674 A | 10/1997 | Bolanos et al. |
| 5,680,981 A | 10/1997 | Mililli et al. |
| 5,680,982 A | 10/1997 | Schulze et al. |
| 5,690,675 A | 11/1997 | Sawyer et al. |
| 5,692,668 A | 12/1997 | Schulze et al. |
| 5,695,506 A | 12/1997 | Pike et al. |

(56) References Cited

U.S. PATENT DOCUMENTS

| | | |
|---|---|---|
| 5,695,524 A | 12/1997 | Kelley et al. |
| 5,702,447 A | 12/1997 | Walch et al. |
| 5,704,534 A | 1/1998 | Huitema et al. |
| 5,713,505 A | 2/1998 | Huitema |
| 5,713,896 A | 2/1998 | Nardella |
| 5,715,987 A | 2/1998 | Kelley et al. |
| 5,716,366 A | 2/1998 | Yates |
| 5,720,753 A | 2/1998 | Sander et al. |
| 5,725,529 A | 3/1998 | Nicholson et al. |
| 5,728,110 A | 3/1998 | Vidal et al. |
| 5,728,116 A | 3/1998 | Rosenman |
| 5,730,757 A | 3/1998 | Benetti et al. |
| 5,735,848 A | 4/1998 | Yates et al. |
| 5,738,474 A | 4/1998 | Blewett |
| 5,755,726 A | 5/1998 | Pratt et al. |
| 5,759,171 A | 6/1998 | Coelho et al. |
| 5,779,130 A | 7/1998 | Alesi et al. |
| 5,782,397 A | 7/1998 | Koukline |
| 5,785,713 A | 7/1998 | Jobe |
| 5,788,698 A | 8/1998 | Savornin |
| 5,810,811 A | 9/1998 | Yates et al. |
| 5,823,066 A | 10/1998 | Huitema et al. |
| 5,829,662 A | 11/1998 | Allen et al. |
| 5,830,121 A | 11/1998 | Enomoto et al. |
| 5,849,023 A | 12/1998 | Mericle |
| 5,849,028 A | 12/1998 | Chen |
| 5,855,311 A | 1/1999 | Hamblin et al. |
| 5,861,005 A | 1/1999 | Kontos |
| 5,865,361 A | 2/1999 | Milliman et al. |
| 5,876,401 A | 3/1999 | Schulze et al. |
| 5,891,156 A | 4/1999 | Gessner et al. |
| 5,893,813 A | 4/1999 | Yamamoto |
| 5,895,396 A | 4/1999 | Day et al. |
| 5,906,607 A | 5/1999 | Taylor et al. |
| 5,911,721 A | 6/1999 | Nicholson et al. |
| 5,918,791 A | 7/1999 | Sorrentino et al. |
| 5,928,222 A | 7/1999 | Kleinerman |
| 5,944,717 A | 8/1999 | Lee et al. |
| 5,944,736 A | 8/1999 | Taylor et al. |
| 5,954,259 A | 9/1999 | Viola et al. |
| 5,961,521 A | 10/1999 | Roger |
| 5,964,394 A | 10/1999 | Robertson |
| 5,968,044 A | 10/1999 | Nicholson et al. |
| 5,976,171 A | 11/1999 | Taylor |
| 5,980,518 A | 11/1999 | Carr et al. |
| 5,980,548 A | 11/1999 | Evans et al. |
| 5,991,355 A | 11/1999 | Dahlke |
| 5,991,650 A | 11/1999 | Swanson et al. |
| 5,992,724 A | 11/1999 | Snyder |
| 5,997,552 A | 12/1999 | Person et al. |
| 6,004,335 A | 12/1999 | Vaitekunas et al. |
| 6,007,550 A | 12/1999 | Wang et al. |
| 6,010,054 A | 1/2000 | Johnson et al. |
| 6,013,077 A | 1/2000 | Harwin |
| 6,015,417 A | 1/2000 | Reynolds, Jr. |
| 6,017,354 A | 1/2000 | Culp et al. |
| 6,030,410 A | 2/2000 | Zurbrugg |
| 6,032,849 A | 3/2000 | Mastri et al. |
| 6,039,731 A | 3/2000 | Taylor et al. |
| 6,051,007 A | 4/2000 | Hogendijk et al. |
| 6,063,078 A | 5/2000 | Wittkampf |
| 6,063,095 A | 5/2000 | Wang et al. |
| 6,077,246 A | 6/2000 | Kullas et al. |
| 6,079,606 A | 6/2000 | Milliman et al. |
| 6,080,150 A | 6/2000 | Gough |
| 6,083,242 A | 7/2000 | Cook |
| 6,090,123 A | 7/2000 | Culp et al. |
| 6,092,422 A | 7/2000 | Binnig et al. |
| 6,109,500 A | 8/2000 | Alli et al. |
| 6,113,592 A | 9/2000 | Taylor |
| 6,123,702 A | 9/2000 | Swanson et al. |
| H1904 H | 10/2000 | Yates et al. |
| 6,126,058 A | 10/2000 | Adams et al. |
| 6,126,651 A | 10/2000 | Mayer |
| 6,127,811 A | 10/2000 | Shenoy et al. |
| 6,132,425 A | 10/2000 | Gough |
| 6,165,169 A | 12/2000 | Panescu et al. |
| 6,166,538 A | 12/2000 | D'Alfonso |
| 6,179,840 B1 | 1/2001 | Bowman |
| 6,187,009 B1 | 2/2001 | Herzog et al. |
| 6,187,019 B1 | 2/2001 | Stefanchik et al. |
| 6,190,401 B1 | 2/2001 | Green et al. |
| 6,193,501 B1 | 2/2001 | Masel et al. |
| 6,202,914 B1 | 3/2001 | Geiste et al. |
| 6,217,573 B1 | 4/2001 | Webster |
| 6,228,534 B1 | 5/2001 | Takeuchi et al. |
| 6,231,565 B1 | 5/2001 | Tovey et al. |
| 6,236,874 B1 | 5/2001 | Devlin et al. |
| 6,237,604 B1 | 5/2001 | Burnside et al. |
| 6,241,139 B1 | 6/2001 | Milliman et al. |
| 6,245,065 B1 | 6/2001 | Panescu et al. |
| 6,248,117 B1 | 6/2001 | Blatter |
| 6,250,532 B1 | 6/2001 | Green et al. |
| 6,258,111 B1 | 7/2001 | Ross et al. |
| 6,264,086 B1 | 7/2001 | McGuckin, Jr. |
| 6,264,087 B1 | 7/2001 | Whitman |
| 6,264,653 B1 | 7/2001 | Falwell |
| 6,281,471 B1 | 8/2001 | Smart |
| 6,288,534 B1 | 9/2001 | Starkweather et al. |
| 6,290,701 B1 | 9/2001 | Enayati |
| 6,293,943 B1 | 9/2001 | Panescu et al. |
| 6,295,330 B1 | 9/2001 | Skog et al. |
| 6,315,184 B1 | 11/2001 | Whitman |
| 6,329,778 B1 | 12/2001 | Culp et al. |
| 6,330,965 B1 | 12/2001 | Milliman et al. |
| 6,346,104 B2 | 2/2002 | Daly et al. |
| 6,355,066 B1 | 3/2002 | Kim |
| 6,364,884 B1 | 4/2002 | Bowman et al. |
| 6,387,092 B1 | 5/2002 | Burnside et al. |
| 6,388,240 B2 | 5/2002 | Schulz et al. |
| 6,402,766 B2 | 6/2002 | Bowman et al. |
| H2037 H | 7/2002 | Yates et al. |
| 6,412,279 B1 | 7/2002 | Coleman et al. |
| 6,425,903 B1 | 7/2002 | Voegele |
| 6,436,097 B1 | 8/2002 | Nardella |
| 6,436,107 B1 | 8/2002 | Wang et al. |
| 6,436,110 B2 | 8/2002 | Bowman et al. |
| 6,443,973 B1 | 9/2002 | Whitman |
| 6,447,517 B1 | 9/2002 | Bowman |
| 6,461,372 B1 | 10/2002 | Jensen et al. |
| 6,478,210 B2 | 11/2002 | Adams et al. |
| 6,497,707 B1 | 12/2002 | Bowman et al. |
| 6,505,768 B2 | 1/2003 | Whitman |
| 6,515,273 B2 | 2/2003 | Al-Ali |
| 6,524,316 B1 | 2/2003 | Nicholson et al. |
| 6,533,157 B1 | 3/2003 | Whitman |
| 6,540,751 B2 | 4/2003 | Enayati |
| 6,544,273 B1 | 4/2003 | Harari et al. |
| 6,554,852 B1 | 4/2003 | Oberlander |
| 6,562,071 B2 | 5/2003 | Jarvinen |
| 6,578,579 B2 | 6/2003 | Burnside et al. |
| 6,601,748 B1 | 8/2003 | Fung et al. |
| 6,601,749 B2 | 8/2003 | Sullivan et al. |
| 6,602,252 B2 | 8/2003 | Mollenauer |
| 6,611,793 B1 | 8/2003 | Burnside et al. |
| 6,616,821 B2 | 9/2003 | Broadley et al. |
| 6,629,986 B1 | 10/2003 | Ross et al. |
| 6,651,669 B1 | 11/2003 | Burnside |
| 6,656,177 B2 | 12/2003 | Truckai et al. |
| 6,669,073 B2 | 12/2003 | Milliman et al. |
| 6,669,705 B2 | 12/2003 | Westhaver et al. |
| 6,696,008 B2 | 2/2004 | Brandinger |
| 6,698,643 B2 | 3/2004 | Whitman |
| 6,699,177 B1 | 3/2004 | Wang et al. |
| 6,716,233 B1 | 4/2004 | Whitman |
| 6,736,085 B1 | 5/2004 | Esnouf |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |

(56) References Cited

U.S. PATENT DOCUMENTS

| | | |
|---|---|---|
| 6,849,071 B2 | 2/2005 | Whitman et al. |
| 6,861,639 B2 | 3/2005 | Al-Ali |
| 6,872,214 B2 | 3/2005 | Sonnenschein et al. |
| 6,899,538 B2 | 5/2005 | Matoba |
| 6,900,004 B2 | 5/2005 | Satake |
| 6,905,057 B2 | 6/2005 | Swayze et al. |
| 6,926,636 B2 | 8/2005 | Luper |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,979,328 B2 | 12/2005 | Baerveldt et al. |
| 6,981,628 B2 | 1/2006 | Wales |
| 6,981,941 B2 | 1/2006 | Whitman et al. |
| 6,988,649 B2 | 1/2006 | Shelton, IV et al. |
| 7,000,819 B2 | 2/2006 | Swayze et al. |
| 7,032,798 B2 | 4/2006 | Whitman et al. |
| 7,044,353 B2 | 5/2006 | Mastri et al. |
| 7,048,687 B1 | 5/2006 | Reuss et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,083,075 B2 | 8/2006 | Swayze et al. |
| 7,097,089 B2 | 8/2006 | Marczyk |
| 7,111,769 B2 | 9/2006 | Wales et al. |
| 7,118,564 B2 | 10/2006 | Ritchie et al. |
| 7,122,029 B2 | 10/2006 | Koop et al. |
| 7,128,253 B2 | 10/2006 | Mastri et al. |
| 7,128,254 B2 | 10/2006 | Shelton, IV et al. |
| 7,140,528 B2 | 11/2006 | Shelton, IV |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,186,966 B2 | 3/2007 | Al-Ali |
| 7,193,519 B2 | 3/2007 | Root et al. |
| 7,217,269 B2 | 5/2007 | El-Galley et al. |
| 7,220,232 B2 | 5/2007 | Suorsa et al. |
| 7,240,817 B2 | 7/2007 | Higuchi |
| 7,241,270 B2 | 7/2007 | Horzewski et al. |
| 7,246,734 B2 | 7/2007 | Shelton, IV |
| 7,303,108 B2 | 12/2007 | Shelton, IV |
| 7,328,828 B2 | 2/2008 | Ortiz et al. |
| 7,335,169 B2 | 2/2008 | Thompson et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,416,101 B2 | 8/2008 | Shelton, IV et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,431,188 B1 | 10/2008 | Marczyk |
| 7,431,189 B2 | 10/2008 | Shelton, IV et al. |
| 7,434,715 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,348 B2 | 1/2009 | Marczyk |
| 7,487,899 B2 | 2/2009 | Shelton, IV et al. |
| 7,549,563 B2 | 6/2009 | Mather et al. |
| 7,552,854 B2 | 6/2009 | Wixey et al. |
| 7,556,185 B2 | 7/2009 | Viola |
| 7,568,603 B2 | 8/2009 | Shelton, IV et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,648,055 B2 | 1/2010 | Marczyk |
| 7,670,334 B2 | 3/2010 | Hueil et al. |
| 7,694,809 B2 | 4/2010 | Garbini et al. |
| 7,721,931 B2 | 5/2010 | Shelton, IV et al. |
| 7,740,159 B2 | 6/2010 | Shelton, IV et al. |
| 7,753,248 B2 | 7/2010 | Viola |
| 7,757,925 B2 | 7/2010 | Viola et al. |
| 7,766,207 B2 | 8/2010 | Mather et al. |
| 7,766,210 B2 | 8/2010 | Shelton, IV et al. |
| 7,770,775 B2 | 8/2010 | Shelton, IV et al. |
| 7,784,663 B2 | 8/2010 | Shelton, IV |
| 7,815,090 B2 | 10/2010 | Marczyk |
| 7,823,760 B2 | 11/2010 | Zemlok et al. |
| 7,845,534 B2 | 12/2010 | Viola et al. |
| 7,870,989 B2 | 1/2011 | Viola et al. |
| 7,886,953 B2 | 2/2011 | Schwemberger et al. |
| 7,887,530 B2 | 2/2011 | Zemlok et al. |
| 7,905,897 B2 | 3/2011 | Whitman et al. |
| 7,909,221 B2 | 3/2011 | Viola et al. |
| 7,922,063 B2 | 4/2011 | Zemlok et al. |
| 7,931,660 B2 | 4/2011 | Aranyi et al. |
| 7,950,560 B2 | 5/2011 | Zemlok et al. |
| 7,955,352 B2 | 6/2011 | McEwen et al. |
| 8,006,885 B2 | 8/2011 | Marczyk |
| 8,006,887 B2 | 8/2011 | Marczyk |
| 8,011,551 B2 | 9/2011 | Marczyk et al. |
| 8,020,742 B2 | 9/2011 | Marczyk |
| 8,025,199 B2 | 9/2011 | Whitman et al. |
| 8,038,044 B2 | 10/2011 | Viola |
| 8,052,024 B2 | 11/2011 | Viola et al. |
| 8,066,721 B2 | 11/2011 | Kortenbach et al. |
| 8,074,858 B2 | 12/2011 | Marczyk |
| 8,092,493 B2 | 1/2012 | Marczyk |
| 8,128,645 B2 | 3/2012 | Sonnenschein et al. |
| 8,132,705 B2 | 3/2012 | Viola et al. |
| 8,157,150 B2 | 4/2012 | Viola et al. |
| 8,186,555 B2 | 5/2012 | Shelton, IV et al. |
| 8,201,721 B2 | 6/2012 | Zemlok et al. |
| 8,210,412 B2 | 7/2012 | Marczyk |
| 8,240,536 B2 | 8/2012 | Marczyk |
| 8,240,537 B2 | 8/2012 | Marczyk |
| 8,267,924 B2 | 9/2012 | Zemlok et al. |
| 8,328,823 B2 | 12/2012 | Aranyi et al. |
| 8,348,125 B2 | 1/2013 | Viola et al. |
| 8,685,004 B2 | 4/2014 | Zemlock et al. |
| 9,192,381 B2 | 11/2015 | Marczyk |
| 9,364,222 B2 | 6/2016 | Zemlok et al. |
| 9,370,360 B2 | 6/2016 | Marczyk |
| 9,370,361 B2 | 6/2016 | Viola et al. |
| 9,433,415 B2 | 9/2016 | Marczyk et al. |
| 9,480,492 B2 | 11/2016 | Aranyi et al. |
| 9,585,659 B2 | 3/2017 | Viola et al. |
| 10,130,361 B2 * | 11/2018 | Yates ................... A61B 17/068 |
| 10,271,844 B2 * | 4/2019 | Valentine ......... A61B 17/07207 |
| 10,492,788 B2 * | 12/2019 | Swayze ............... A61B 17/115 |
| 10,492,814 B2 | 12/2019 | Snow et al. |
| 10,722,222 B2 | 7/2020 | Aranyi |
| 2002/0103489 A1 | 8/2002 | Ku |
| 2002/0111641 A1 | 8/2002 | Peterson et al. |
| 2002/0165541 A1 | 11/2002 | Whitman |
| 2003/0090201 A1 | 5/2003 | Peng |
| 2003/0114851 A1 | 6/2003 | Truckai et al. |
| 2003/0120306 A1 | 6/2003 | Burbank et al. |
| 2004/0232201 A1 | 11/2004 | Wenchell et al. |
| 2005/0006429 A1 | 1/2005 | Wales et al. |
| 2005/0010235 A1 | 1/2005 | VanDusseldorp |
| 2005/0131390 A1 | 6/2005 | Heinrich et al. |
| 2005/0139636 A1 | 6/2005 | Schwemberger et al. |
| 2005/0177176 A1 | 8/2005 | Gerbi et al. |
| 2005/0192609 A1 | 9/2005 | Whitman et al. |
| 2005/0247753 A1 | 11/2005 | Kelly et al. |
| 2006/0000867 A1 | 1/2006 | Shelton et al. |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0219563 A1 | 9/2007 | Voegele |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |

(56) References Cited

U.S. PATENT DOCUMENTS

| | | |
|---|---|---|
| 2008/0135600 A1 | 6/2008 | Hiranuma et al. |
| 2008/0169329 A1 | 7/2008 | Shelton et al. |
| 2008/0185419 A1 | 8/2008 | Smith et al. |
| 2008/0197167 A1 | 8/2008 | Viola et al. |
| 2008/0255413 A1 | 10/2008 | Zemlok et al. |
| 2008/0255607 A1 | 10/2008 | Zemlok |
| 2009/0018624 A1 | 1/2009 | Levinson et al. |
| 2009/0090201 A1 | 4/2009 | Viola |
| 2009/0090763 A1 | 4/2009 | Zemlok et al. |
| 2010/0200636 A1 | 8/2010 | Zemlok et al. |
| 2010/0312257 A1 | 12/2010 | Aranyi |
| 2010/0320254 A1 | 12/2010 | Zemlok et al. |
| 2011/0034910 A1 | 2/2011 | Ross et al. |
| 2011/0062211 A1 | 3/2011 | Ross et al. |
| 2011/0168757 A1 | 7/2011 | Viola et al. |
| 2011/0172681 A1 | 7/2011 | Aranyi et al. |
| 2011/0190738 A1 | 8/2011 | Zemlok et al. |
| 2011/0301579 A1 | 12/2011 | Marczyk et al. |
| 2011/0303735 A1 | 12/2011 | Marczyk |
| 2012/0055972 A1 | 3/2012 | Marczyk |
| 2012/0074197 A1 | 3/2012 | Marczyk |
| 2012/0175400 A1 | 7/2012 | Viola et al. |
| 2012/0193393 A1 | 8/2012 | Viola et al. |
| 2012/0198288 A1 | 8/2012 | Njo et al. |
| 2012/0220989 A1 | 8/2012 | Zemlok et al. |
| 2012/0223121 A1 | 9/2012 | Viola et al. |
| 2012/0241494 A1 | 9/2012 | Marczyk |
| 2012/0277790 A1 | 11/2012 | Zemlok et al. |
| 2012/0298718 A1 | 11/2012 | Marczyk |
| 2012/0298720 A1 | 11/2012 | Marczyk |
| 2016/0270780 A1* | 9/2016 | Hall ................... A61B 90/98 |
| 2018/0125601 A1* | 5/2018 | Cabrera ............ A61B 17/1155 |
| 2018/0353186 A1* | 12/2018 | Mozdzierz ......... A61B 17/072 |
| 2018/0360460 A1* | 12/2018 | Mozdzierz ......... A61B 90/3476 |
| 2019/0090877 A1* | 3/2019 | Fox ................... A61B 90/03 |
| 2019/0099181 A1* | 4/2019 | Shelton, IV ........ A61B 90/03 |
| 2019/0125459 A1* | 5/2019 | Shelton, IV ........ A61B 90/30 |
| 2019/0183592 A1* | 6/2019 | Shelton, IV ........ A61B 17/282 |
| 2019/0200997 A1* | 7/2019 | Shelton, IV ........ G16H 40/63 |
| 2019/0200998 A1* | 7/2019 | Shelton, IV ........ A61B 90/98 |
| 2019/0201020 A1* | 7/2019 | Shelton, IV ........ A61B 90/361 |
| 2019/0201104 A1* | 7/2019 | Shelton, IV ........ A61B 34/25 |
| 2019/0206564 A1* | 7/2019 | Shelton, IV ........ H04L 67/566 |
| 2020/0093487 A1* | 3/2020 | Baber ................. A61B 90/92 |
| 2021/0386424 A1* | 12/2021 | Abramek ........... A61B 17/072 |
| 2022/0015766 A1* | 1/2022 | Kollar ............... A61B 17/1155 |

FOREIGN PATENT DOCUMENTS

| | | |
|---|---|---|
| EP | 0537570 A2 | 4/1993 |
| EP | 0647431 A2 | 4/1995 |
| EP | 0738501 A1 | 10/1996 |
| EP | 0770354 A1 | 5/1997 |
| EP | 1070487 A2 | 1/2001 |
| EP | 1201196 A1 | 5/2002 |
| EP | 1658817 A1 | 5/2006 |
| EP | 1813203 A2 | 8/2007 |
| EP | 3714810 A1 | 9/2020 |
| FR | 2 849 589 A1 | 7/2004 |
| WO | 9414129 A1 | 6/1994 |
| WO | 9729694 A1 | 8/1997 |
| WO | 9740760 A1 | 11/1997 |
| WO | 9837825 A1 | 9/1998 |
| WO | 1999/52489 A1 | 10/1999 |
| WO | 0234140 A2 | 5/2002 |
| WO | 03026511 A1 | 4/2003 |
| WO | 03030743 A2 | 4/2003 |
| WO | 2004032760 A2 | 4/2004 |
| WO | 2007030753 A2 | 3/2007 |
| WO | 2007/114868 A2 | 10/2007 |
| WO | 2007118179 A2 | 10/2007 |
| WO | 2007014355 A3 | 4/2009 |
| WO | 2009143092 A1 | 11/2009 |
| WO | 2020014056 A1 | 1/2020 |

OTHER PUBLICATIONS

Abridged Data Sheet, "DeepCover Secure Authenticator with 1-Wire SHA-256 and 512-Bit User EEPROM", Maxim Integrated Products, Inc. pp. 1-4; 42; Dec. 2012.

Data Sheet "DS28E15—1—Sire SHA-256 Secure Authenticator with 512-Bit User EEPROM"; IC-ON-LINE, Electronic Component Manufacturers, pp. 1-2; Aug. 2013.

International Search Report and Written Opinion dated Sep. 23, 2022 issued in corresponding PCT Appln. No. PCT/IB2022/055255.

* cited by examiner

HANDHELD ELECTROMECHANICAL SURGICAL SYSTEM

BACKGROUND

1. Technical Field

The present disclosure relates to surgical devices. More specifically, the present disclosure relates to handheld electromechanical surgical systems for performing surgical clamping, stapling, and cutting procedures.

2. Background of Related Art

One type of surgical device is a circular clamping, stapling, and cutting device. Circular staplers are used in a surgical procedure to adjoin hollow structures such as colon and rectum that were previously transected, or similar procedures. Conventional circular clamping, cutting and stapling instruments include a pistol or linear grip-styled structure having an elongated shaft extending therefrom and a staple cartridge supported on the distal end of the elongated shaft. In this instance, a physician may insert an anvil assembly of the circular stapling instrument into a rectum of a patient and maneuver the anvil assembly up the colonic tract of the patient toward the transected rectum portions. The physician may also insert the remainder of the circular stapling instrument (including the cartridge assembly) through an incision and toward the transected rectum portions. The anvil and cartridge assemblies are approximated toward one another and staples are ejected from the cartridge assembly toward the anvil assembly to form the staples in tissue to affect an end-to-end anastomosis, and an annular knife is fired to core a portion of the clamped tissue portions. After the end-to-end anastomosis has been effected, the circular stapling apparatus is removed from the surgical site.

A number of surgical device manufacturers have developed product lines with powered drive systems for operating and/or manipulating the surgical device. In many instances the surgical devices, i.e., powered surgical staplers, include a powered handle assembly and an adapter assembly, which are reusable, and a disposable staple cartridge assembly that is selectively connected to the adapter assembly prior to use. The adapter assembly includes multiple transmission assemblies, e.g., drive shafts, which transmit actuation from the powered handle to the disposable staple cartridge. The powered surgical staplers operate in three sequences, namely, clamping, stapling, and cutting. Clamping approximates tissue grasped between an anvil and a cartridge assembly and compresses the tissue. This sequence prepares the tissue to receive staples. There is a need for a powered surgical stapler having an automated clamping process configured to achieve adequate tissue relaxation and dissipation of stored energy.

SUMMARY

The present disclosure provides a powered circular stapler is configured to operate in three sequences, namely, clamping, stapling, and cutting to form an anastomosis by connecting two portions of a structure (e.g., intestine, colon, etc.). During the clamping sequence an anvil is approximated toward a cartridge assembly to compress tissue, i.e., two separated portions of a colon. The powered circular stapler is configured to execute a clamping algorithm, which may be embodied as software instructions executed by a controller or processor. The clamping algorithm allows for clamping tissue to a gap distance smaller than the eventual clamp distance to leverage tissue hysteresis and promote relaxation of the tissue before applying staples, i.e., stapling sequence. The clamping algorithm brings the anvil proximally of a preset clamp gap position by a predetermined distance during clamping and then extends distally of the clamp gap position before indicating to the user that the powered circular stapler is ready to fire, i.e., proceed to the stapling sequence. It is envisioned that the clamping algorithm according to the present disclosure may be implemented any powered stapling device, including linear staplers and robotic staplers.

According to one embodiment of the present disclosure, a surgical device is disclosed. The surgical device includes a power source and a motor coupled to the power source. The device also includes a controller configured to control the motor. The device further includes a reload including a plurality of staples and an anvil assembly movable relative to the reload by the motor. The controller is configured to control the motor to move the anvil assembly from a distal clamp position to a proximal clamp position and then distally from the proximal clamp position to reduce the clamp force.

According to another embodiment of the present disclosure, a surgical device is disclosed. The surgical device includes a handle assembly having: a power source, a motor coupled to the power source, and a controller configured to control the motor. The device also includes an adapter assembly configured to selectively couple to the handle assembly. The adapter assembly includes a clamping transmission assembly movable by the motor. The device also includes a reload configured to selectively couple to a distal portion of the adapter assembly, the reload including a plurality of staples ejectable from the reload. The device further includes an anvil assembly selectively couplable to the distal portion of the adapter assembly and movable relative to the reload. The controller is further configured to control the motor to move the clamping transmission assembly to move the anvil assembly from a distal clamp position to a proximal clamp position and then distally from the proximal clamp position to reduce the clamp force.

Implementations of the above embodiments of the surgical device may include one or more of the following features. According to one aspect of the above embodiment, the controller may be further configured to maintain the anvil assembly at the distal clamp position for a preset period of time. The preset period of time may be from about 1 second to about 12 seconds. The controller may be further configured to verify that the anvil assembly was maintained at the distal clamp position for the preset period of time and to enable a stapling sequence based on the confirmation. The surgical device may include a display. The display may be configured to show a progress bar representing the preset period. The surgical device may also include a sensor configured to measure the force imparted by the anvil assembly. The controller may be further configured to control the motor moving the anvil assembly between the distal clamp position and the proximal clamp position based on the measured force.

According to a further embodiment of the present disclosure, a method for controlling a surgical stapler is disclosed. The method includes moving an anvil assembly from a distal clamp position to a proximal clamp position and maintaining the anvil assembly at the proximal clamp position for a preset period of time. The method also includes reversing the anvil assembly to move the anvil assembly from the proximal clamp position to the distal clamp position and ejecting staples from a reload while the anvil assembly is in the distal clamp position.

Implementations of the above method may include one or more of the following features. According to one aspect of the above embodiment, the method may also include moving an anvil assembly from a fully open position to an intermediate position; and measuring force imparted by the anvil assembly. The method may further include moving the anvil assembly from the intermediate position to the distal clamp position based on the measured force. The method may also include moving the anvil assembly between the distal clamp position and the proximal clamp position based on the measured force.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 1:
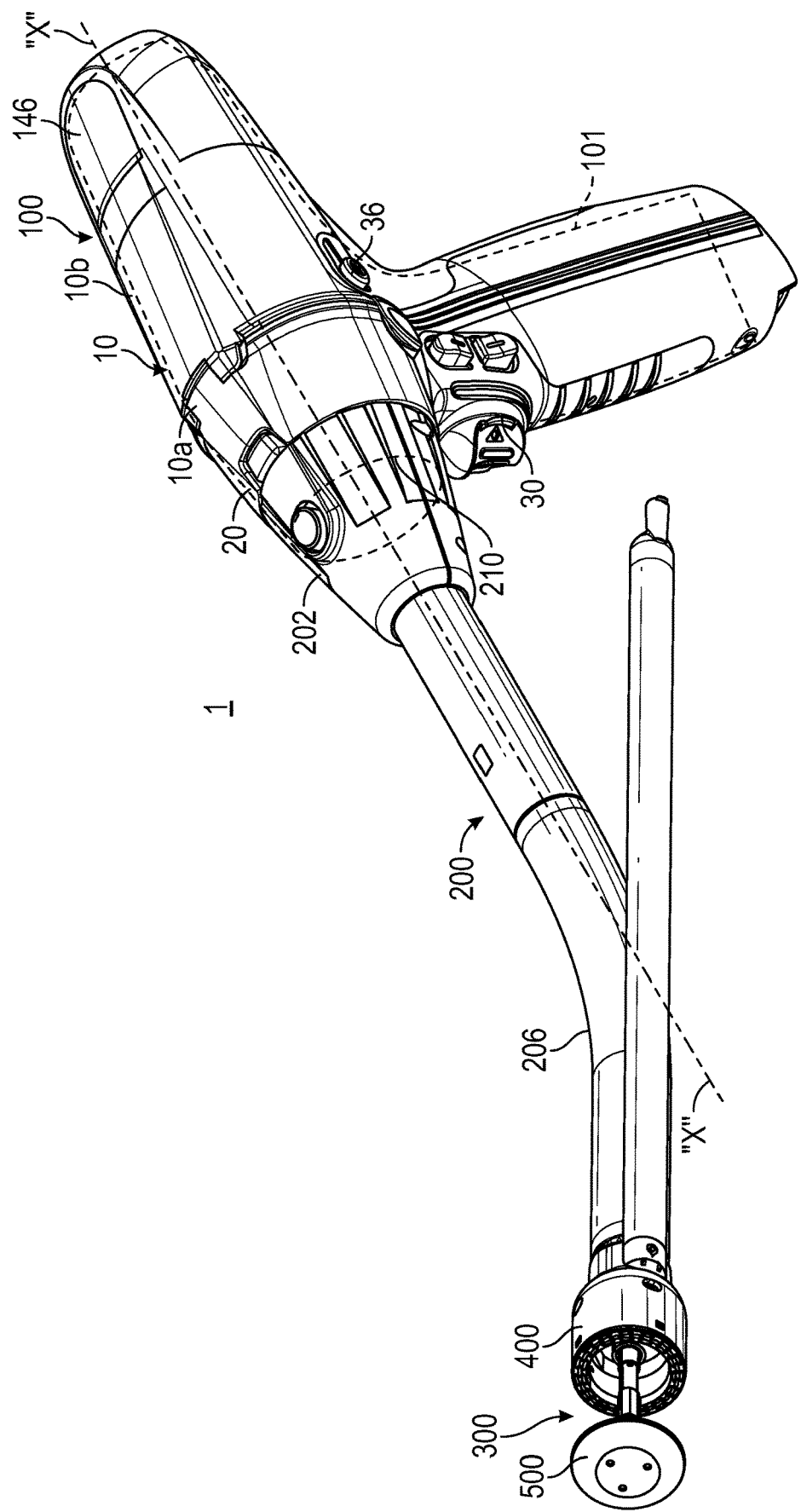
FIG. 1 is a perspective view of a handheld surgical instrument including a handle assembly, an adapter assembly, and an end effector, according to an embodiment of the present disclosure.

Embodiments of the presently disclosed surgical devices, and adapter assemblies for surgical devices and/or handle assemblies are described in detail with reference to the drawings, in which like reference numerals designate identical or corresponding elements in each of the several views. As used herein the term "distal" refers to that portion of the surgical instrument, or component thereof, farther from the user, while the term "proximal" refers to that portion of the surgical instrument, or component thereof, closer to the user.

The present disclosure provides a powered circular stapler 1 having a handle assembly, an adapter assembly coupled to the handle assembly, and an end effector coupled to the adapter assembly. The stapler allows for full, independent control of three functions: clamping, stapling, and cutting. This allows certain portions of the stapler to adapt if the tissue presents a non-ideal situation.

FIG. 1 illustrates a surgical device, such as, for example, a powered circular stapler 1 for forming end-to-end anastomosis ("EEA"), including a handle assembly 100, which is configured for selective connection with an adapter assembly 200. The adapter assembly 200 is configured for selective connection with an end effector 300, which includes a reload 400 and an anvil assembly 500. The end effector 300 is configured to produce a surgical effect on tissue of a patient, namely, forming an anastomosis by connecting two portions of a structure (e.g., intestine, colon, etc.) by clamping, stapling, and cutting tissue grasped within the end effector 300.

The handle assembly 100 includes a power handle 101 and an outer shell housing 10 configured to selectively receive and encase power handle 101. The shell housing 10 includes a distal half-section 10a and a proximal half-section 10b pivotably connected to distal half-section 10a. When joined, distal and proximal half-sections 10a, 10b define a shell cavity therein in which power handle 101 is disposed.

Distal and proximal half-sections 10a, 10b of shell housing 10 are divided along a plane that traverses a longitudinal axis "X" of adapter assembly 200. Distal half-section 10a of shell housing 10 defines a connecting portion 20 configured to accept a corresponding drive coupling assembly 210 (FIG. 3) of adapter assembly 200. Distal half-section 10a of shell housing 10 supports a toggle control button 30. Toggle control button 30 is capable of being actuated in four directions (e.g., a left, right, up and down).

Figure 2:
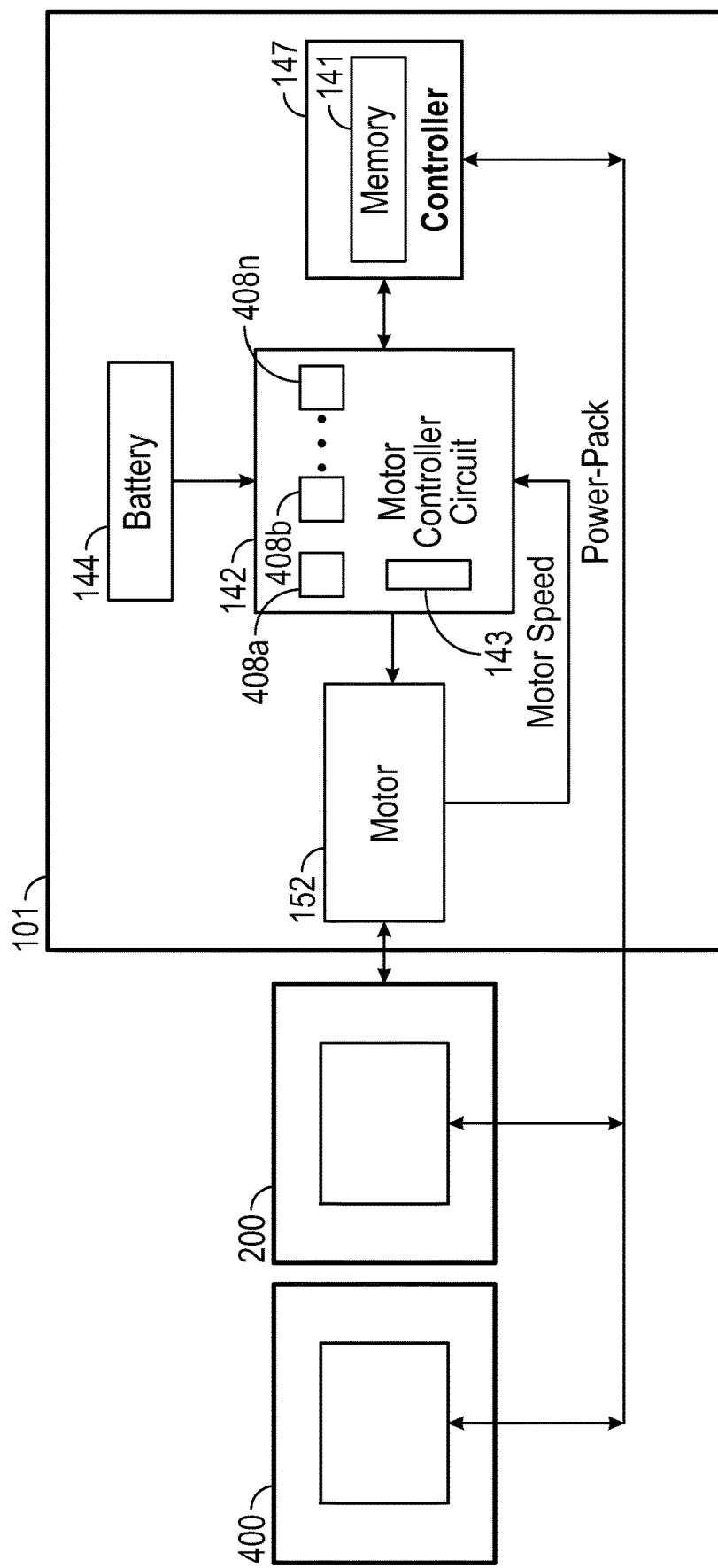
FIG. 2 is a schematic diagram of the handle assembly, the adapter assembly, and the end effector of FIG. 1.

With reference to FIGS. 1 and 2, the power handle 101 includes a main controller circuit board 142, a rechargeable battery 144 configured to supply power to any of the electrical components of handle assembly 100, and a plurality of motors 152 coupled to the battery 144. The power handle 101 also includes a display 146. In embodiments, the motors 152 may be coupled to any suitable power source configured to provide electrical energy to the motor 152, such as an AC/DC transformer. Each of the motors 152 is coupled a motor controller 143 which controls the operation of the corresponding motor 152 including the flow of electrical energy from the battery 144 to the motor 152. A main controller 147 is provided that controls the power handle 101. The main controller 147 is configured to execute software instructions embodying algorithms disclosed herein, such as clamping, stapling, and cutting algorithms which control operation of the power handle 101.

The motor controller 143 includes a plurality of sensors 408a ... 408n configured to measure operational states of the motor 152 and the battery 144. The sensors 408a-n include a strain gauge 408b and may also include voltage sensors, current sensors, temperature sensors, telemetry sensors, optical sensors, and combinations thereof. The sensors 408a-408n may measure voltage, current, and other electrical properties of the electrical energy supplied by the battery 144. The sensors 408a-408n may also measure angular velocity (e.g., rotational speed) as revolutions per minute (RPM), torque, temperature, current draw, and other operational properties of the motor 152. The sensor 408a also includes an encoder configured to count revolutions or other indicators of the motor 152, which is then use by the main controller 147 to calculate linear movement of components movable by the motor 152. Angular velocity may be determined by measuring the rotation of the motor 152 or a drive shaft (not shown) coupled thereto and rotatable by the motor 152. The position of various axially movable drive shafts may also be determined by using various linear sensors disposed in or in proximity to the shafts or extrapolated from the RPM measurements. In embodiments, torque may be calculated based on the regulated current draw of the motor 152 at a constant RPM. In further embodiments, the motor controller 143 and/or the main controller 147 may measure time and process the above-described values as a function of time, including integration and/or differentiation, e.g., to determine the rate of change in the measured values. The main controller 147 is also configured to determine distance traveled of various components of the adapter assembly 200 and/or the end effector 300 by counting revolutions of the motor 152.

The motor controller 143 is coupled to the main controller 147, which includes a plurality of inputs and outputs for interfacing with the motor controller 143. In particular, the main controller 147 receives measured sensor signals from the motor controller 143 regarding operational status of the motor 152 and the battery 144 and, in turn, outputs control signals to the motor controller 143 to control the operation of the motor 152 based on the sensor readings and specific algorithm instructions. The main controller 147 is also configured to accept a plurality of user inputs from a user interface (e.g., switches, buttons, touch screen, etc. coupled to the main controller 147).

The main controller 147 is also coupled to a memory 141. The memory 141 may include volatile (e.g., RAM) and non-volatile storage configured to store data, including software instructions for operating the power handle 101. The main controller 147 is also coupled to the strain gauge 408b of the adapter assembly 200 using a wired or a wireless connection and is configured to receive strain measurements from the strain gauge 408b which are used during operation of the power handle 101.

The power handle 101 includes a plurality of motors 152 each including a respective motor shaft (not explicitly shown) extending therefrom and configured to drive a respective transmission assembly. Rotation of the motor shafts by the respective motors function to drive shafts and/or gear components of adapter assembly 200 in order to perform the various operations of handle assembly 100. In particular, motors 152 of power handle 101 are configured to drive shafts and/or gear components of adapter assembly 200 in order to selectively extend/retract a trocar member 274 (FIG. 4) of a trocar assembly 270 of adapter assembly 200. Extension/retraction of the trocar member 274 opens/closes end effector 300 (when anvil assembly 500 is connected to trocar member 274 of trocar assembly 270), fire an annular array of staples 423 of reload 400, and move an annular knife (not explicitly shown) of reload 400.

The reload 400 includes a storage device 402 configured to store operating parameters of the reload 400 including starting clamping force, maximum clamping force, a force factor, and the like. Each type of reload 400 may have a corresponding starting clamping force, which the main controller 147 may obtain automatically by reading the starting clamping force value from the storage device 402 and/or set manually by the user by selecting either the type of the reload 400 or the clamping force directly. Starting clamping force may be any suitable threshold from about 100 pounds to about 200 pounds, in embodiments, the target clamping force may be approximately 150 pounds. In embodiments, a 33 mm sized reload 400 may have a clamping force of about 150 lbs.

Figure 3:
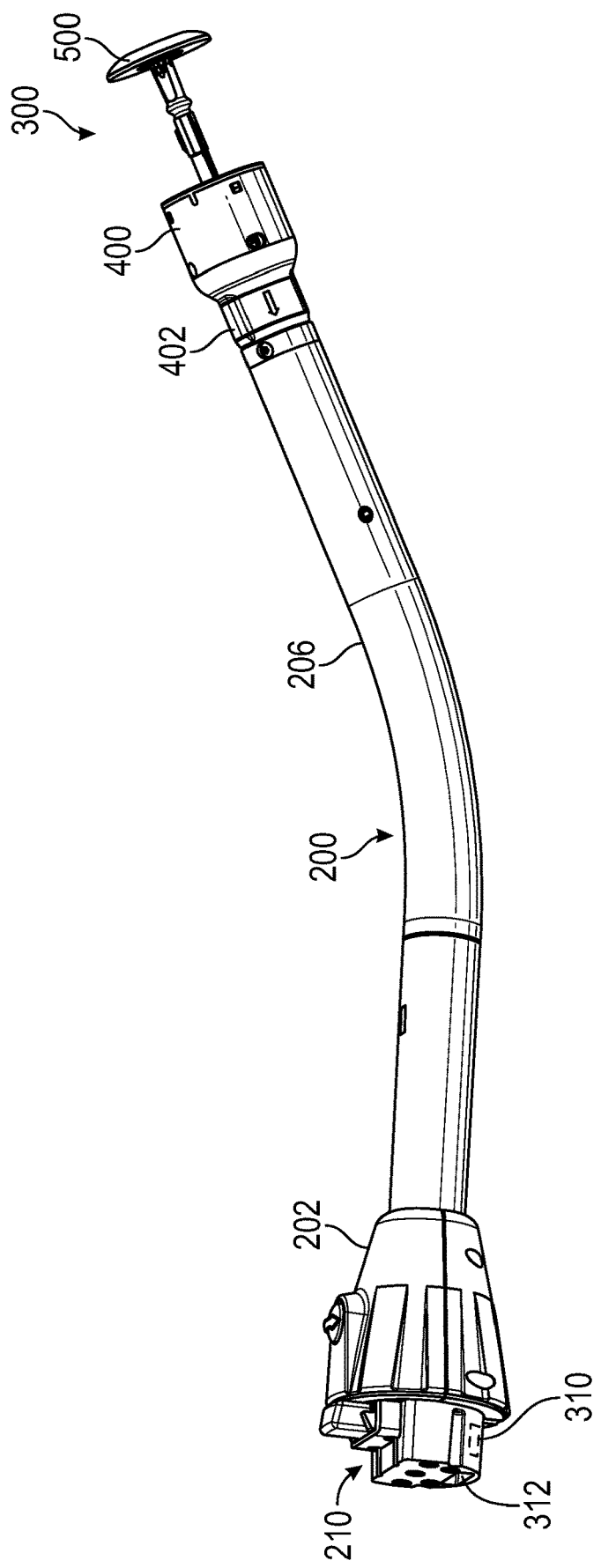
FIG. 3 is a side perspective view of the adapter assembly and the end effector, an annular reload and an anvil assembly, attached to the adapter assembly of FIG. 1 according to an embodiment of the present disclosure.
Figure 4:
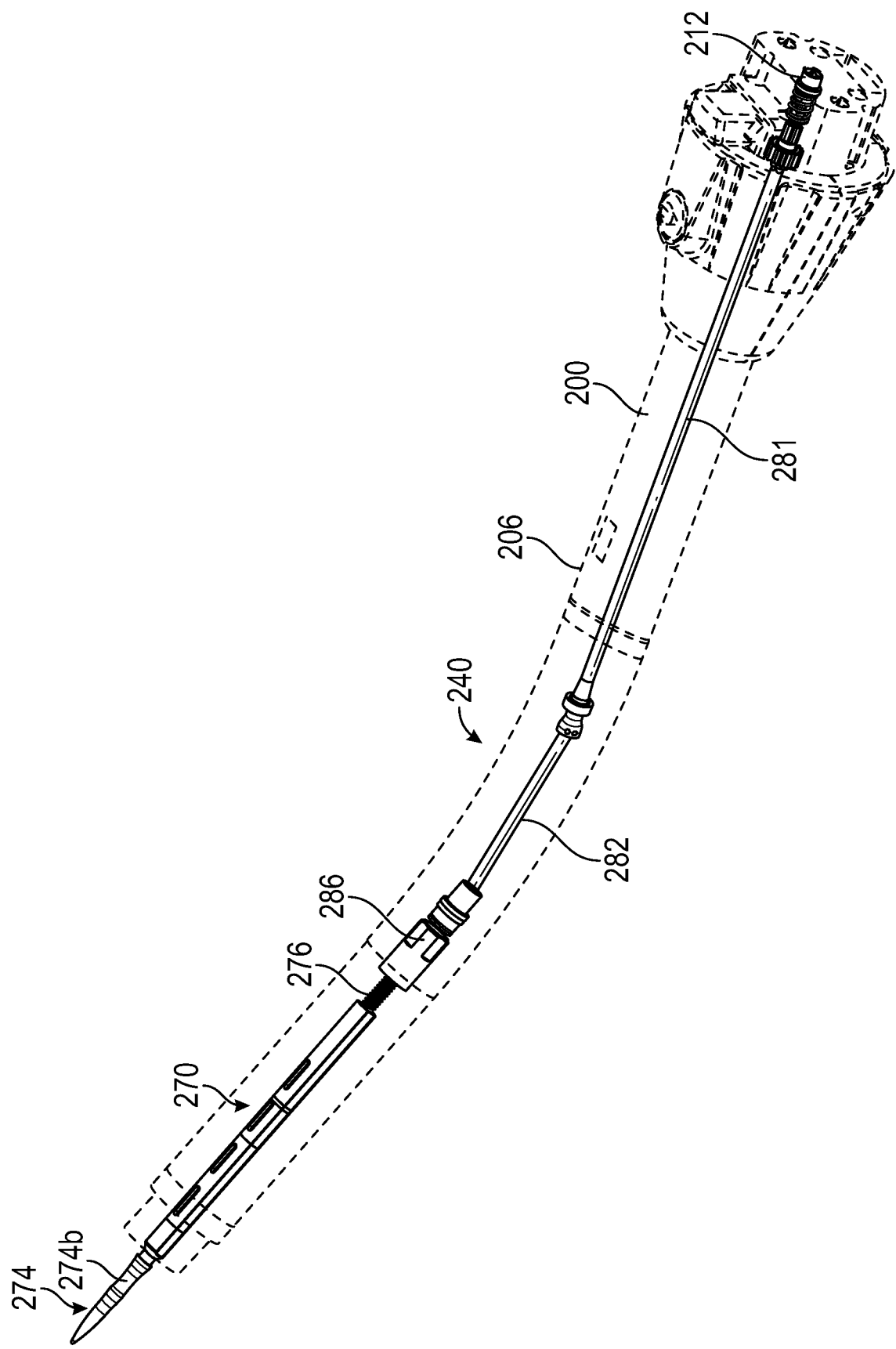
FIG. 4 is a perspective view of a clamping transmission assembly disposed within the adapter assembly of FIG. 1, shown partially in phantom.

Turning now to FIGS. 3 and 4, adapter assembly 200 includes an outer knob housing 202 and an outer tube 206 extending from a distal end of knob housing 202. Knob housing 202 and outer tube 206 are configured and dimensioned to house the components of adapter assembly 200. The knob housing 202 includes an electrical connector 312 and a storage device 310 coupled thereto. The storage device 310 is configured to store various operating parameters pertaining to the adapter assembly 200. Adapter assembly 200 is configured to convert rotation of coupling shafts (not explicitly shown) of handle assembly 100 into axial translations useful for operating trocar assembly 270 of adapter assembly 200, anvil assembly 500, and/or staple driver 430 or knife assembly (not explicitly shown) of reload 400.

Adapter assembly 200 further includes the trocar assembly 270 removably supported in a distal end of outer tube 206. Trocar assembly 270 includes a trocar member 274 and a drive screw 276 operably received within trocar member 274 for axially moving trocar member 274 relative to outer tube 206. A distal end 274b of trocar member 274 is configured to selectively engage anvil assembly 500, such that axial movement of trocar member 274, via a rotation of drive screw 276, results in a concomitant axial movement of anvil assembly 500.

With reference to FIG. 4, a clamping transmission assembly 240 includes first rotatable proximal drive shaft 212 coupled to one of the motors 152, a second rotatable proximal drive shaft 281, a rotatable distal drive shaft 282, and a coupling member 286, each of which are supported within the outer tube 206 of adapter assembly 200. Clamping transmission assembly 240 functions to extend/retract trocar member 274 of trocar assembly 270 of adapter assembly 200, and to open/close the anvil assembly 510 when anvil assembly 510 is connected to trocar member 274.

Figure 5:
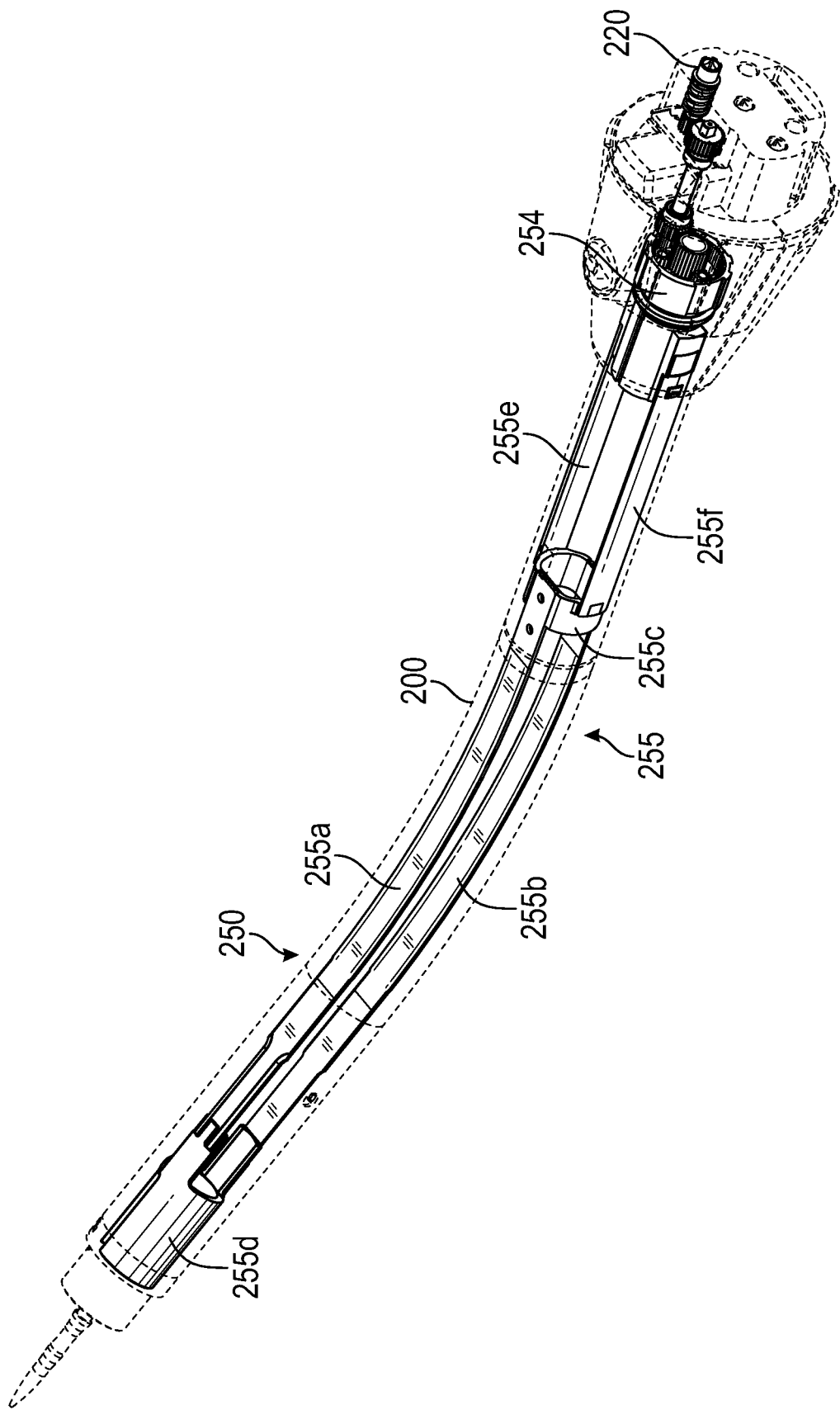
FIG. 5 is a perspective view of a stapling transmission assembly disposed within the adapter assembly of FIG. 1, shown partially in phantom.

With reference to FIG. 5, the adapter assembly 200 includes a stapling transmission assembly 250 for interconnecting one of the motors 152 and a second axially translatable drive member of reload 400, wherein the stapling transmission assembly 250 converts and transmits a rotation of one of the motors 152 to an axial translation of an outer flexible band assembly 255 of adapter assembly 200, and in turn, the staple driver 430 of reload 400 to fire staples 423 from the reload 400 and against anvil assembly 510.

The stapling transmission assembly 250 of adapter assembly 200 includes the outer flexible band assembly 255 secured to staple driver coupler 254. A second rotatable proximal drive shaft 220 is coupled to one of the motors 152 and is configured to actuate that staple driver coupler 254, which converts rotational movement into longitudinal movement. Outer flexible band assembly 255 includes first and second flexible bands 255a, 255b laterally spaced and connected at proximal ends thereof to a support ring 255c and at distal ends thereof to a proximal end of a distal pusher 255d. Each of first and second flexible bands 255a, 255b is attached to support ring 255c and distal pusher 255d. Outer flexible band assembly 255 further includes first and second connection extensions 255e, 255f extending proximally from support ring 255c. First and second connection extensions 255e, 255f are configured to operably connect outer flexible band assembly 255 to staple driver coupler 254 of stapling transmission assembly 250.

Figure 6:
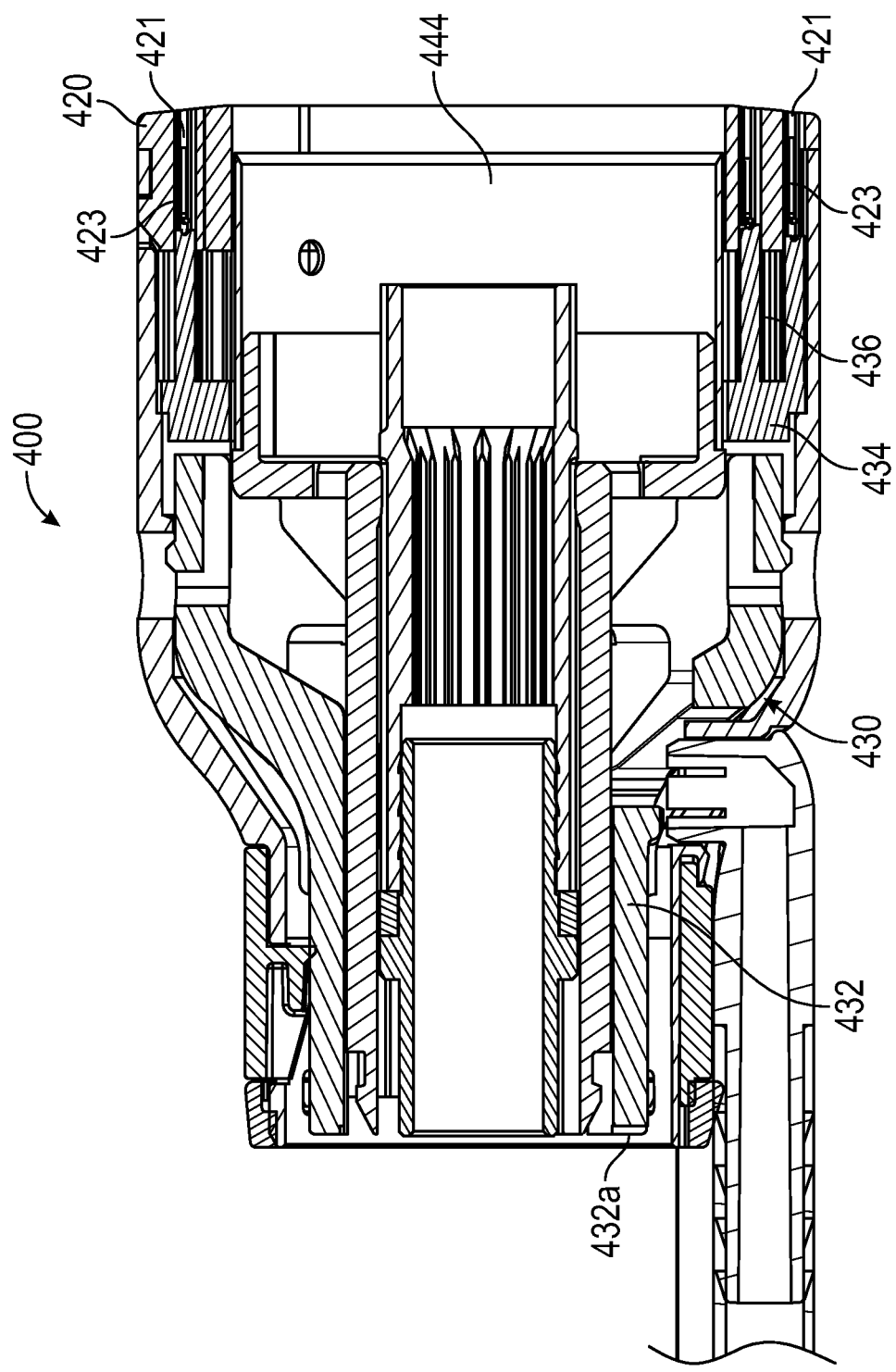
FIG. 6 is a cross-sectional view of a reload of the end effector of FIG. 1.

With reference to FIG. 6, staple driver 430 of reload 400 includes a staple cartridge 420 having a driver adapter 432 and a driver 434. A proximal end 432a of driver adapter 432 is configured for selective contact and abutment with distal pusher 255d of outer flexible band assembly 255 of stapling transmission assembly 250 of adapter assembly 200. In operation, during distal advancement of outer flexible band assembly 255, as described above, distal pusher 255d of outer flexible band assembly 255 contacts proximal end 432a of driver adapter 432 to advance driver adapter 432 and driver 434 from a first or proximal position to a second or distal position. Driver 434 includes a plurality of driver members 436 aligned with staple pockets 421 of staple cartridge 420 for contact with staples 423. Accordingly, advancement of driver 434 relative to staple cartridge 420 causes ejection of the staples 423 from staple cartridge 420.

Forces during an actuation of trocar member 274, closing of end effector 300 (e.g., a retraction of anvil assembly 500 relative to reload 400), and ejecting staples 423 from the reload 400 may be measured by the strain gauge 408b in order to monitor and control various processes, such as firing of staples 423 from reload 400; monitor forces during a firing and formation of the staples 423 as the staples 423 are being ejected from reload 400; optimize formation of the staples 423 (e.g., staple crimp height) as the staples 423 are being ejected from reload 400 for different indications of tissue; and monitor and control a firing of the annular knife of reload 400.

Figure 7:
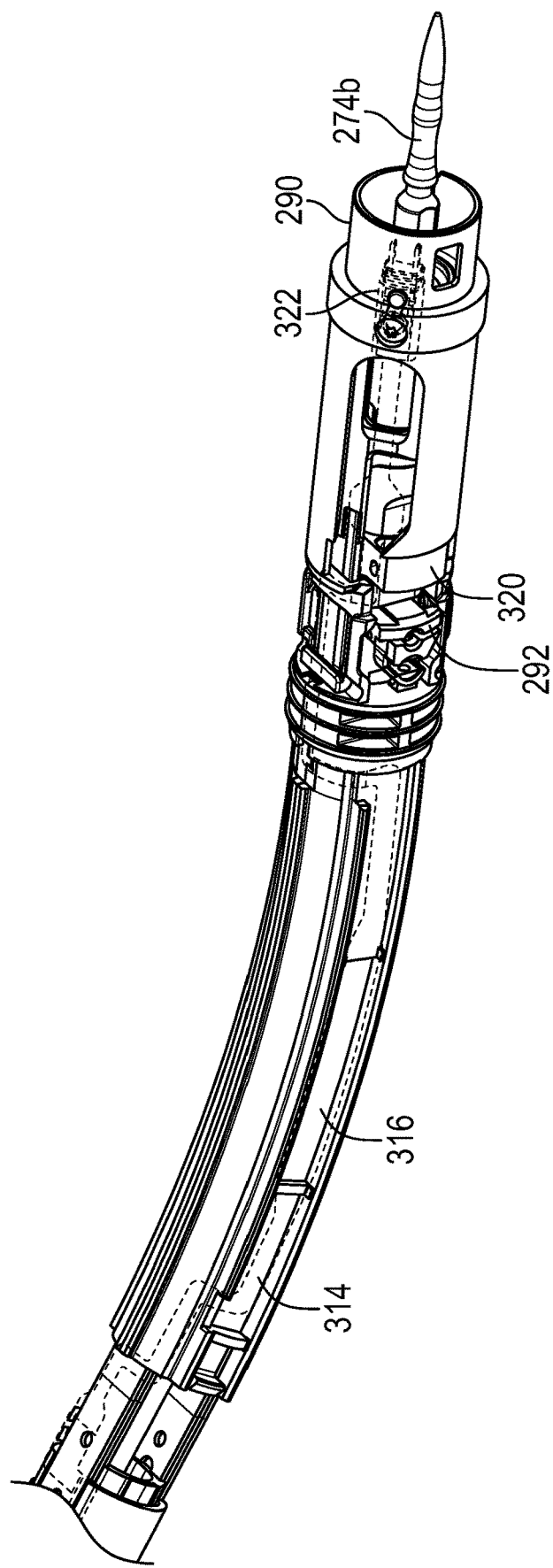
FIG. 7 is a perspective view of the adapter assembly, shown partially disassembled, with a strain gauge assembly.
Figure 10:
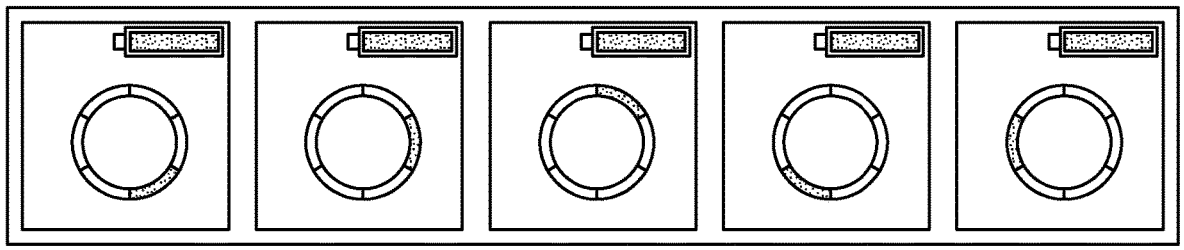
FIG. 10 shows a graphical user interface illustrating holding of the anvil assembly for a preset time to achieve tissue hysteresis.

With reference to FIG. 7, the strain gauge 408b of adapter assembly 200 is disposed within a strain gauge housing 320. The strain gauge 408b measures and monitors the retraction of trocar member 274 as well as the ejection and formation of the staples 423 from the reload 400. During the closing of end effector 300, when anvil assembly 500 contacts tissue, an obstruction, a tissue-contacting surface of the reload 400, staple ejection, or the like, a reaction force is exerted on anvil assembly 500 which is in a generally distal direction. This distally directed reaction force is communicated from anvil assembly 500 to the strain gauge 408b. The strain gauge 408b then communicates signals to main controller circuit board 142 of power handle 101 of handle assembly 100. Graphics are then displayed on the display 146 of handle assembly 100 to provide the user with real-time status information as shown in FIG. 10.

The trocar assembly 270 is axially and rotationally fixed within outer tube 206 of adapter assembly 200. With reference to FIG. 6, adapter assembly 200 includes a support block 292 fixedly disposed within outer tube 206. The strain gauge housing 320 is disposed between the support block 292 and a connector sleeve 290. The reload 400 is removably coupled to the connector sleeve 290.

In operation, strain gauge 408b of adapter assembly 200 measures and monitors the retraction of trocar member 274, which passes through the strain gauge 408b. The strain gauge 408b of adapter assembly 200 also measures and monitors ejection of the staples 423 from the reload 400, since the first and second flexible bands 255a, 255b also pass through the strain gauge 408b. During clamping, stapling and cutting, a reaction force is exerted on anvil assembly 500 and the reload 400, which is communicated to support block 292, which then communicates the reaction force to a strain sensor of the strain gauge 408b.

Strain sensor of strain gauge 408b may be any device configured to measure strain (a dimensionless quantity) on an object that it is adhered to (e.g., support block 292), such that, as the object deforms, a metallic foil of the strain sensor is also deformed, causing an electrical resistance thereof to change, which change in resistance is then used to calculate loads experienced by trocar assembly 270. Strain gauge 408b provides a closed-loop feedback to a firing/clamping load exhibited by first, second and third force/rotation transmitting/converting assemblies.

Strain sensor of strain gauge 408b then communicates signals to main controller circuit board 142. Graphics are then displayed on display 146 of handle assembly 100 to provide the user with real-time information related to the status of the firing of handle assembly 100. Strain gauge 408b is also electrically connected to the electrical connector 312 (FIG. 3) via proximal and distal harness assemblies 314, 316.

For further details regarding the construction and operation of the circular stapler and its components, reference may be made to International Application Publication No. PCT/US2019/040440, filed on Jul. 3, 2019, the entire contents of which being incorporated by reference herein.

The user commences a surgical procedure by positioning the adapter assembly 200, including the trocar member 274 and the anvil assembly 510, within the colorectal or upper gastrointestinal region. The user presses the toggle control button 30 to extend the trocar member 274 until it pierces tissue. During operation, the anvil assembly 500 (after being positioned by surgeon at the tissue site where anastomosis is being performed) is attached to the trocar member 274 and the user begins the clamping process on the tissue interposed between reload 400 and the anvil assembly 500 by pressing on the bottom of the toggle control button 30. After extension of the trocar member 274, the anvil assembly 510 that was previously positioned by surgeon is attached to the trocar member 274. The surgeon then begins the clamping process on the tissue interposed between reload 400 and the anvil assembly 510 by pressing on the bottom portion of the toggle control button 30.

During clamping, the anvil assembly 500 is retracted toward the reload 400 until reaching a preset, fully clamped position (i.e., the fourth position 604). The preset clamped position varies for each of the different types of reloads (e.g., the distance is about 29 mm for 25 mm reloads). While clamping, the strain gauge 408b continuously provides measurements to the main controller 147 on the force imparted on the trocar member 274 as it moves the anvil assembly 500 to clamp tissue between the anvil assembly 500 and the reload 400.

Figure 8:
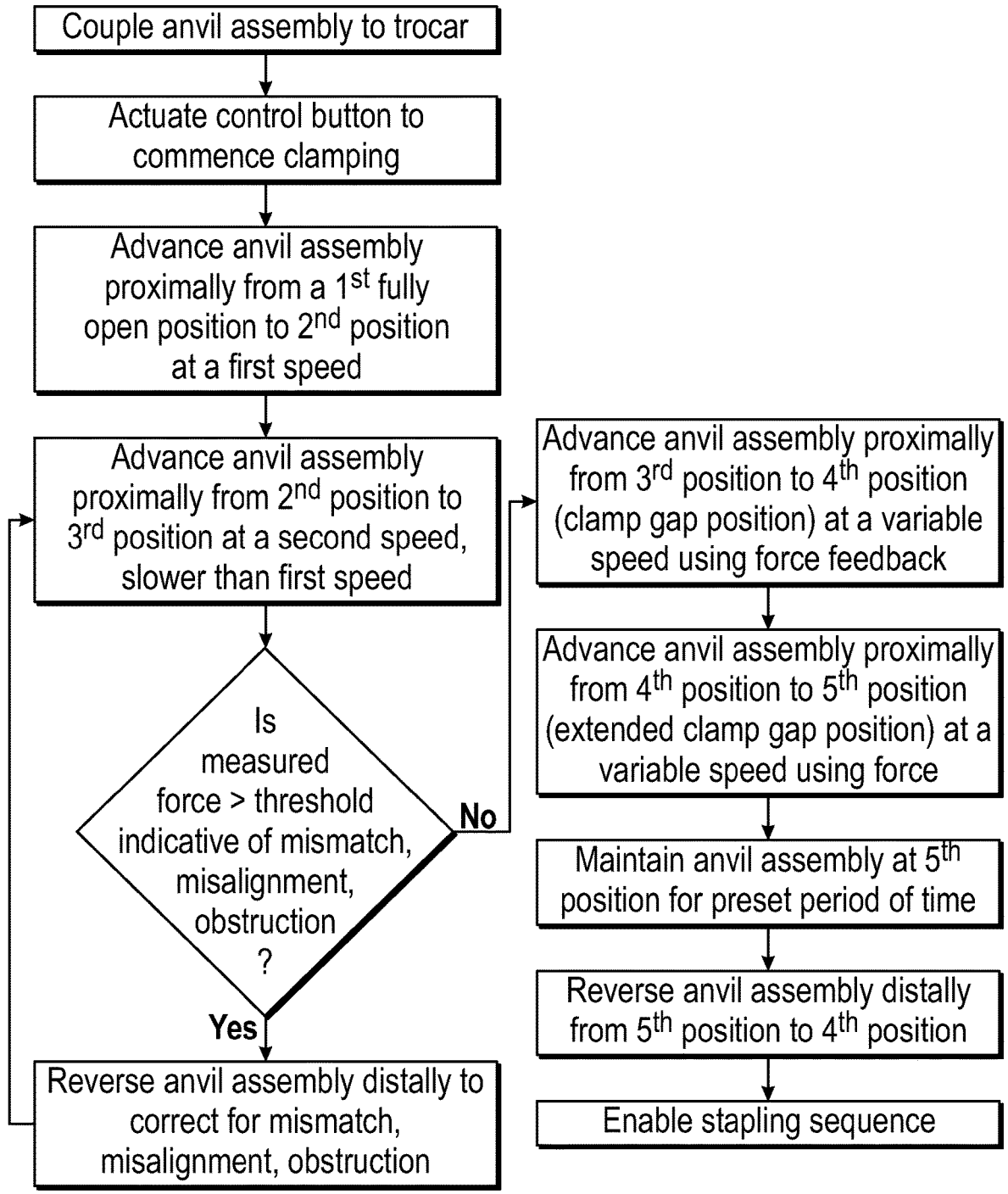
FIG. 8 is a method for controlling the surgical instrument of FIG. 1 during the stapling sequence according to an embodiment of the present disclosure.
Figure 9:
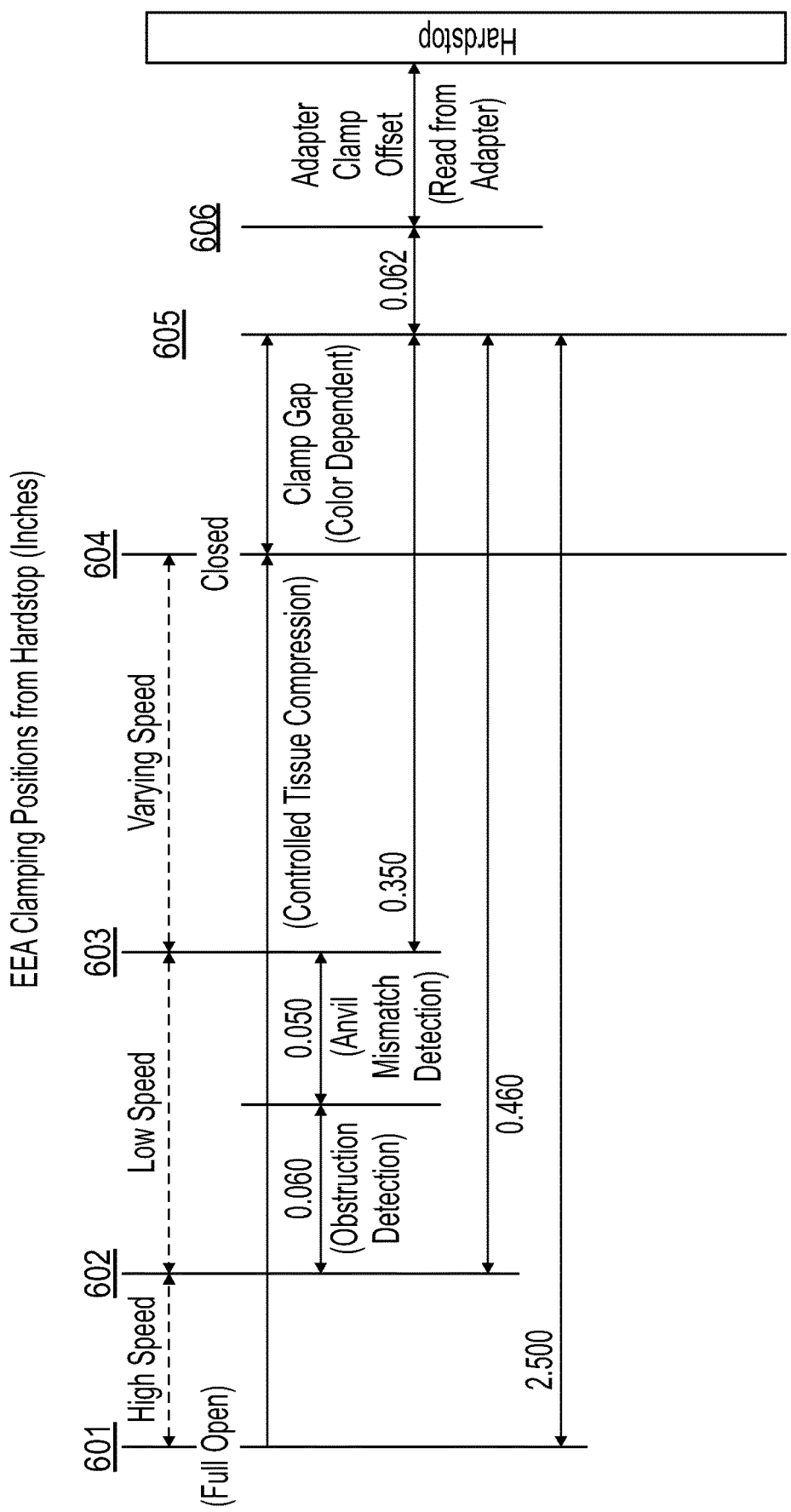
FIG. 9 is a schematic diagram illustrating travel distance and speed of the anvil assembly and a corresponding motor during a clamping sequence performed by the handheld surgical device of FIG. 1 according to an embodiment of the present disclosure.

FIG. 8 shows a clamping algorithm according to the present disclosure. With reference to FIG. 9, which schematically illustrates the travel distance and speed of the anvil assembly 500 as it is retracted by the first motor 152. The anvil assembly 500 is retracted, i.e., moved proximally, from a first fully open position 601 at a first speed for a first segment from the fully open position 601 to a second position 602, which is closer to the reload 400. This is done in response to user pressing the toggle control button 30. Thereafter, the anvil assembly 500 traverses proximally along a second segment from the second position 602 to a third position 603 at the second speed, which is slower than the first speed. As the anvil assembly 500 is traversing the second segment, the main controller 147 continuously verifies whether the measured force is within predefined parameters to determine if the measured force exceeds a high force threshold limit prior to reaching a starting compression distance. This measurement is used to detect obstruction, a mismatch between the anvil assembly 500 and the reload 400, and/or misalignment of the anvil assembly 500 with the reload 400. If the force is higher than the high force threshold, then the power handle 101 temporarily reverses the clamping transmission assembly 240 to retract the anvil assembly 500 to correct the misalignment. The main controller 147 then reattempts to continue clamping, i.e., moving the anvil assembly 500 proximally toward the reload 400, until a third position 603 is reached. If the third position 603 is not reached within a predetermined period of time, the main controller 147 then issues an error, including an alarm on the display screen 146 prompting the user to inspect the anvil assembly 500. After inspection and clearance of any obstruction, the user may then restart the clamping process.

Once the anvil assembly 500 reaches the third position 603, which is at the end of the second segment, the power handle 101 performs a rotation verification to check position of the anvil assembly 500. Then the main controller 147 commences a controlled tissue compression ("CTC") algorithm. The CTC algorithm has two phases—the first CTC phase starts from the third position 603, during which the anvil assembly 500 is driven proximally to a fourth position 604 (i.e., a clamp gap position) at a varying speed based on a measured force.

Advancement of the anvil assembly 500 between the third position 603 and the fourth position 604 accounts for slow-changing and rapid-changing forces imparted on the tissue during compression with a second-order predictive force filter. As the predicted force approaches the target force, the clamping speed is slowed to prevent over-shoot. When the measured force reaches the target force and the clamp gap has not yet been achieved, clamping is stopped to allow for tissue relaxation. During tissue relaxation, after the measured force falls below the target clamping force, advancement recommences. The force exerted on tissue is derived from the strain measurements by the main controller 147 from the strain gauge 408b. This process continues until the fourth position 604 is reached.

Once the fourth position 604 has been reached, the anvil assembly 500 is advanced proximally to a fifth position 605, (i.e., extended clamp gap position). Before advancing the anvil assembly 500 to the fifth position 605, after reaching the fourth position 604, the anvil assembly 500 may be stopped temporarily, which may be from about 0.5 seconds to about 2 seconds. The distance between the fourth position 604 to the fifth position 605 may be from about 0.002" to about 0.02". The anvil assembly 500 is advanced proximally to the fifth position 605 based on measured force in the same manner as the clamping between the third position 603 and the fourth position 604. In particular, the anvil assembly 500 may be advanced from the fourth position 604 to the fifth position 605 using the same force feedback as used to advance to the fourth position 604.

Once the fifth position 605 is reached, a notification that the fifth position 605 has been reached may be displayed on the display 146 and audio tones may be output by the power handle 101. The anvil assembly 500 is maintained at the fifth position 605 for a predetermined period of time, which may be from about 1 second to about 12 seconds and in embodiments, may be from about 2 seconds to about 6 seconds. The anvil assembly 500 maintains a preset force on the tissue, which may be from about 80 lbs to about 150 lbs, which in embodiments may be about 105 lbs. Progress of the anvil assembly 500 being held at the sixth position 606 may be illustrated using a progress bar or circle 700 as shown in FIG. 10, in which each segment of the circle 700 may represent a time segment depending on the total preset time. Each segment may be from about 150 milliseconds to about 2 milliseconds.

Figure 11:
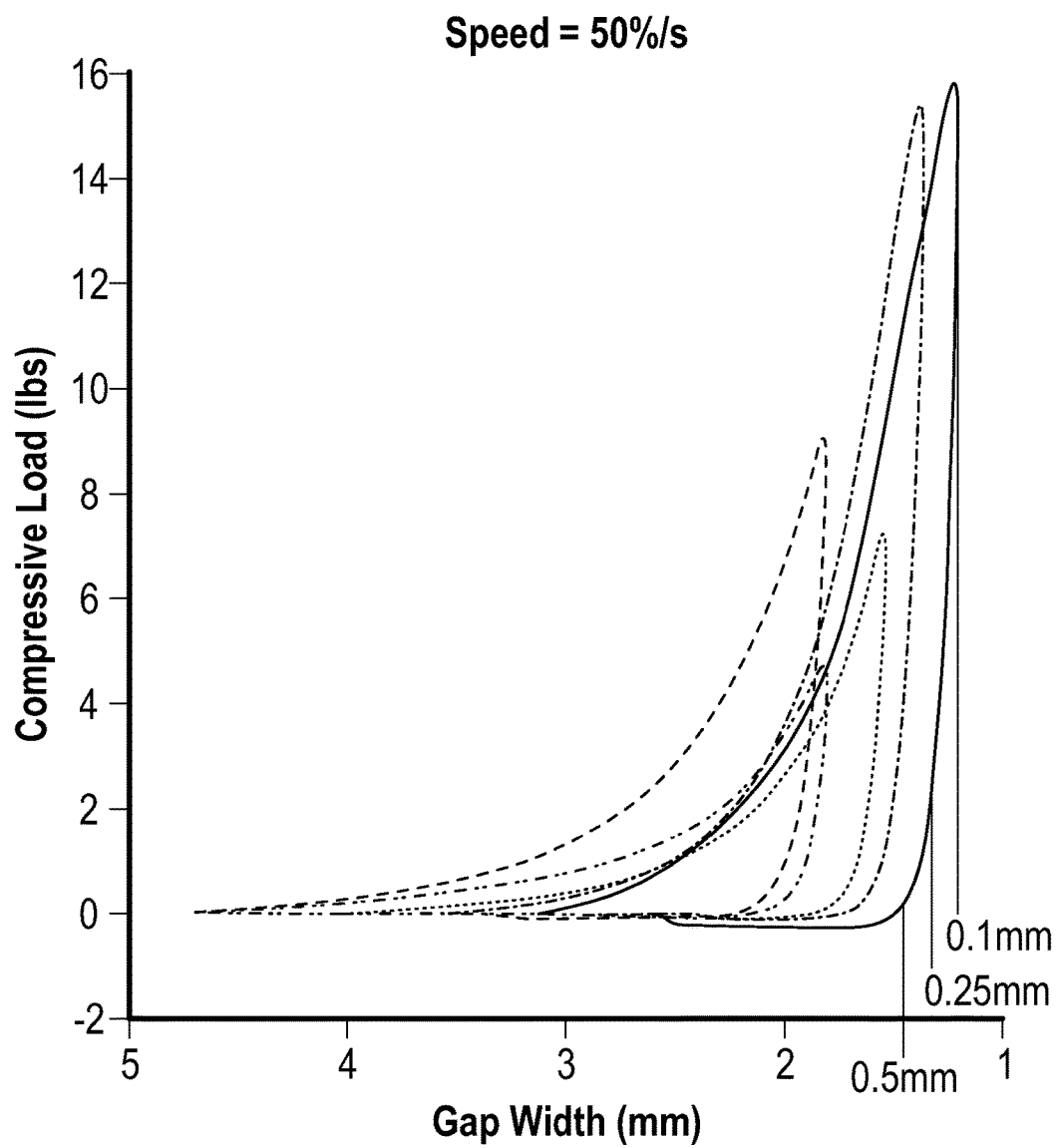
FIG. 11 shows plots of compressive loads as a function of gap width illustrating decrease in the load exerted on tissue in response to extension of the anvil assembly from the reload according to an embodiment of the present disclosure.

Once the preset time has expired, the anvil assembly 500 is moved distally from the sixth position 606 to the fifth position 605. Maintaining the preset force for the preset time, followed by relaxation, i.e., distal of the anvil assembly back to the fifth position 605, results in decreased clamp force by leveraging tissue hysteresis, which is a material phenomenon whereby the stored mechanical energy is dissipated more rapidly during unclamping than during clamping. Thus, a relatively small amount of unclamping can induce a pronounced decrease in internal loads, which may be about 0 lbs with only 12.5% unclamping as shown in FIG. 11, which shows plots of compressive loads as a function of gap width. Each of the plots illustrate that as gap distance is increased (i.e., the anvil assembly 500 is moved distally from the fifth position 605 to the fourth position 604), the load is decreased substantially, although the distal movement is very small, which as noted above may be about 0.2".

The disclosed clamping algorithm has the potential to improve clinical outcomes by reducing stored energy in the tissue before stapling, thereby decreasing the likelihood of suboptimal device performance. Internal loads developed in tissue during clamping or compression occur due to the energy that is stored in the tissue during deformation. Tissue hysteresis is utilized to minimize the mechanical load on the tissue prior to stapling. As a result, this the algorithm according to the present disclosure improves staple formation and increase tissue blood perfusion.

The main controller 147 verifies that tissue hysteresis was performed. In embodiments, the main controller 147 may verify that a desired relaxation has occurred based on the measured force. The main controller 147 signals that tissue clamping, including tissue hysteresis was successful. Once clamping is successfully completed, the user initiates the stapling sequence. To initiate stapling sequence, the user presses one of the safety buttons 36 of the power handle 101, which acts as a safety and arms the toggle control button 30, allowing it to commence stapling. The user then presses down on the toggle control button 30, which moves the second rotation transmitting assembly 250 to convert rotation to linear motion and to eject and form staples from circular reload 400.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A surgical device comprising:
a power source;
a motor coupled to the power source;
a controller configured to control the motor;
a reload including a plurality of staples; and
an anvil assembly movable relative to the reload by the motor,
wherein the controller is configured to control the motor to:
move the anvil assembly from a distal clamp position to a proximal clamp position;
maintain the anvil assembly at the proximal clamp position for a preset period of time; and
reverse the anvil assembly to move the anvil assembly distally from the proximal clamp position to achieve tissue hysteresis.

2. The surgical device according to claim 1, wherein the preset period of time is from about 1 second to about 12 seconds.

3. The surgical device according to claim 1, wherein the controller is further configured to confirm that the anvil assembly was maintained at the distal clamp position for the preset period of time and to enable a stapling sequence based on the confirmation.

4. The surgical device according to claim 1, further comprising a display.

5. The surgical device according to claim 4, wherein the display is configured to show a progress bar representing the preset period.

6. The surgical device according to claim 1, further comprising a sensor configured to measure force imparted by the anvil assembly.

7. The surgical device according to claim 6, wherein the controller is further configured to control the motor moving the anvil assembly between the distal clamp position and the proximal clamp position based on the measured force.

8. A surgical device comprising:
a handle assembly including:
a power source;
a motor coupled to the power source; and
a controller configured to control the motor;
an adapter assembly configured to selectively couple to the handle assembly, the adapter assembly including a clamping transmission assembly movable by the motor;
a reload configured to selectively couple to a distal portion of the adapter assembly, the reload including a plurality of staples ejectable from the reload; and
an anvil assembly selectively couplable to the distal portion of the adapter assembly and movable relative to the reload,
wherein the controller is further configured to control the motor to:
move the clamping transmission assembly to move the anvil assembly from a distal clamp position to a proximal clamp position;
maintain the anvil assembly at the proximal clamp position for a preset period of time; and
reverse the anvil assembly to move the anvil assembly distally from the proximal clamp position to achieve tissue hysteresis.

9. The surgical device according to claim 8, wherein the preset period of time is from about 1 second to about 12 seconds.

10. The surgical device according to claim 8, wherein the controller is further configured to confirm that the anvil assembly was maintained at the distal clamp position for the preset period of time and to enable a stapling sequence based on the confirmation.

11. The surgical device according to claim 8, further comprising a display.

12. The surgical device according to claim 11, wherein the display is configured to show a progress bar representing the preset period.

13. The surgical device according to claim 8, further comprising a sensor configured to measure force imparted by the anvil assembly.

14. The surgical device according to claim 13, wherein the controller is further configured to control the motor moving the anvil assembly between the distal clamp position and the proximal clamp position based on the measured force.

15. A method for controlling a surgical stapler, the method comprising:
moving an anvil assembly from a distal clamp position to a proximal clamp position;
maintaining the anvil assembly at the proximal clamp position for a preset period of time;
reversing the anvil assembly to move the anvil assembly from the proximal clamp position to the distal clamp position; and
ejecting staples from a reload while the anvil assembly is in the distal clamp position.

16. The method according to claim 15, further comprising:
moving an anvil assembly from a fully open position to an intermediate position; and
measuring force imparted by the anvil assembly.

17. The method according to claim 16, further comprising:
moving the anvil assembly from the intermediate position to the distal clamp position based on the measured force.

18. The method according to claim 16, further comprising:
moving the anvil assembly between the distal clamp position and the proximal clamp position based on the measured force.

* * * * *